United States Patent [19]

Munkholm

[11] Patent Number: 6,107,099
[45] Date of Patent: Aug. 22, 2000

[54] HYDROPHOBIC FLUORESCENT POLYMER MEMBRANE FOR THE DETECTION OF AMMONIA

[75] Inventor: Christiane Munkholm, Salem, Mass.

[73] Assignee: Bayer Corporation, E. Walpole, Mass.

[21] Appl. No.: 09/455,283

[22] Filed: Dec. 6, 1999

Related U.S. Application Data

[63] Continuation of application No. 08/906,711, Aug. 5, 1997, Pat. No. 6,013,529.

[51] Int. Cl.$^7$ .................................................. G01N 33/00
[52] U.S. Cl. ......................... 436/113; 436/106; 436/164; 436/172; 422/55; 422/82.05; 422/82.08
[58] Field of Search ..................................... 436/106, 111, 436/113, 164, 169, 170, 172, 800; 422/55, 56, 82.05, 82.07, 82.08, 82.11

[56] References Cited

U.S. PATENT DOCUMENTS

| | | | |
|---|---|---|---|
| 4,223,089 | 9/1980 | Anselm et al. | 435/12 |
| 5,005,572 | 4/1991 | Raemer | 128/207.14 |
| 5,173,434 | 12/1992 | Morris | 436/172 |
| 5,330,868 | 7/1994 | Santilli | 430/106 |
| 5,372,784 | 12/1994 | Morris | 422/82.08 |
| 5,387,525 | 2/1995 | Munkholm | 436/111 |
| 5,506,148 | 4/1996 | Munkholm | 436/111 |
| 5,577,137 | 11/1996 | Groger | 385/12 |
| 6,013,529 | 1/2000 | Munkholm | 436/113 |

FOREIGN PATENT DOCUMENTS

| | | |
|---|---|---|
| 0 481 436 | 4/1992 | European Pat. Off. . |
| 0 623 599 | 11/1994 | European Pat. Off. . |
| 0 708 335 A2 | 4/1996 | European Pat. Off. . |
| 195 22 610 | 12/1996 | Germany . |
| WO 94/17388 | 8/1994 | WIPO . |

OTHER PUBLICATIONS

Muller et al. *Proc. SPIE–Int. Soc. Opt. Eng.*, vol. 2388(Advances in Fluorescence Sensing Technology II) pp. 558–567, 1995.

Preininger et al. *Analytica Chimica Acta*, vol. 334, pp. 113–123, Nov. 1996.
* Kar, Satyajit et al. "Fiber Optic Ammonia Sensor for Measuring Synaptic Glutamate and Extracellular Ammonia", *Anal. Chem.* 1992, 64, 2438–2443.
* Meyerhoff, Mark E., "Polymer Membrane Electrode Based Potentiometric Ammonia Gas Sensor", *Anal. Chem.* 1980, 52, 1532–1534.
* Mills, Andrew et al., "Equilibrium Studies on Colorimetric Plastic Film Sensors for Carbon Dioxide", *Anal. Chem.* 1992, 64 1383–1389.
* Ozawa, Satoshi et al., "Ammonia–Gas–Selective Opticfal Sensors Based on Neutral Ionophores", *Anal.. Chem.* 1991, 63, 640–644.
* Rhines, Timothy D., et al., "Determination of Ammonia in Untreated Serum with a Fiber–Optic Ammonia Gas Sensor", *Analytica Chimica Acta*, 231 (1990) 231–235.
* Rhines, Timothy D., et al., "Fiber–Optic Biosensor for Urea Based on Sensing of Ammonia Gas" *Analytica Chimica Acta*, 227 (1989) 387–396.
* Weigl, Bernhard H. ,et al., "Sensitivity Studies on Optical Carbon Dioxide Sensors Based on Ion Pairing", *Sensors and Actuators*, B 28 (1995) 151–156.
* Werner, Tobias et al., "Ammonia–Sensitive Polymer Matrix Employing Immobolized Indicator Ion Pairs", *Analyst*, Jun. 1995, vol. 120, 1627–1631.
* Wolfbeis, Otto S. "Optical Sensing Based on Analyte Recognition by Enzymes, Carriers and Molecular Interactions", *Analytica Chimica Acta*, 250 (1991) 181–201.
* Wolfbeis, Otto S. et al., "Fibre–Optic Flouresing Sensor for Ammonia", *Analytica Chimmica Acta*, 185 (1996) 321–327. *

*Primary Examiner*—Maureen M. Wallenhorst

[57] ABSTRACT

The present invention provides an ammonia sensor including a pH sensitive fluorophore immobilized in a hydrophobic polymer, wherein the fluorophore can react quantitatively with ammonia and the transducing moiety of the fluorophore is neutrally charged when deprotonated. The present invention also provides a method for detecting ammonia using the ammonia sensor and optical sensing devices comprising the ammonia sensor.

3 Claims, 2 Drawing Sheets

HYDROPHOBIC FLUORESCENT POLYMER MEMBRANE FOR THE DETECTION OF AMMONIA

CROSS-REFERENCE TO RELATED APPLICATIONS

This application is a continuation application of, and claims priority from, U.S. application Ser. No. 08/906,711, filed Aug. 5, 1997, now U.S. Pat. No. 6,013,529 issued on Jan. 11, 2000.

BACKGROUND OF THE INVENTION

1. Field of the Invention

The present invention relates to sensors for the detection of ammonia.

2. Description of Related Art

Continuous monitoring of analytes can be accomplished by a number of methods, including those based on electrochemical, calorimetric and fluorometric detection. Ammonia sensors utilizing electrochemical methods take advantage of the fact that at physiologic pH, ammonia is protonated to form ammonium ions, which increase the electrical conductivity of the solution proximal to the electrode.

Colorimetric monitoring is achieved by the detection of color or loss of color using either qualitative visual observation or spectrophotometric measurement of the color intensity. Such colorimetric monitoring has an important limitation: sensitivity of detection. To improve sensitivity, fluorescence-based sensors can be used. However, not all colorimetric assays may have fluorescent equivalents.

Ammonia can be monitored using an optical sensor. The detection of analytes by optical sensors requires the development of fluorescent transducers which are specific for different analytes, coupled to a media or surface capable of transmitting light, such as optical fibers. Optical transducers for the detection of ammonia can be modulated by ammonium or ammonia.

Detection of ammonium requires an ammonium specific ionophore coupled to a chromophore that changes its absorption spectrum upon protonation, and a lipophilic anionic site. As such, sensors based on the detection of ammonium can be expensive and complex.

Detection of ammonia requires a protonated pH sensitive indicator ($IND^+$) which changes its absorption or fluorescence spectrum upon deprotonation:

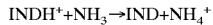
$INDH^+ + NH_3 \rightarrow IND + NH_4^+$

There is also a drawback to designing a sensor based on detection of ammonia: namely the rapid protonation of ammonia at physiologic pH. The $pK_a$ of ammonium is 9.3, which is not a pH that supports maximum enzyme activity.

A fiber-optic fluorescing sensor to detect ammonia was reported by Wolfbeis and Posch (*Anal. Chim. Acta*, 185: 321–327 (1986)). The sensing material was prepared as a buffered emulsion of dyes in an aqueous solution entrapped in a silicone rubber. The ammonia response for this sensor was not always reversible, and the signal intensity was low as the dye was dissolved in aqueous buffers before being prepared as an emulsion in the polymer.

Other methods of detecting ammonia have been to sequester an indicator solution from the sample (Rhines, T. D.; Arnold, M. A., *Anal. Chim. Acta*, 227: 387–396 (1989)) or to use an anionic colorimetric pH indicator paired with a quaternary ammonium cation, which has been solubilized in a silicone elastomer (Werner, T.; Klimant, I.; Wolfbeis, O. S. *Analyst*, 120: 1627–1631 (1995)).

Hydrophobic polymers, optically transparent and permeable to the analyte of interest, are used with optical sensors when the analyte is a vapor or gas and is capable of diffusion into a hydrophobic membrane. A complication arises when hydrophobic polymers are used with certain fluorescent dyes. Sensors for ammonia require a protonated indicator. When combined with a hydrophobic membrane for the detection of ammonia, polyanionic pH indicators, which are the common variety of protonated indicator and the type used in the fluorescent urea sensor described in Rhines and Arnold (*Anal. Chim. Acta*, 231: 231–235 (1990)), do not produce an activated and protonated fluorophore.

While various indicators for ammonia are known, many ammonia sensors exhibit problems with interferences from pH and $CO_2$ effects, low sensitivity, slow response times and reversibility. Additionally, polyanionic pH indicators typically used in the detection of ammonia have not been successfully used in conjunction with hydrophobic polymers. From a manufacturing standpoint, it would therefore be desirable to develop an inexpensive ammonia sensor that has a high sensitivity, fast response time, and is reversible. It would also be advantageous for the sensor to be able to function in conjunction with sensors detecting other analytes.

SUMMARY OF THE INVENTION

The present invention provides an ammonia sensor material comprising a protonated pH sensitive fluorophore immobilized in a hydrophobic polymer, wherein the fluorophore can react quantitatively with ammonia and the transducing moiety of the fluorophore is neutrally charged when deprotonated.

The present invention also provides a method for detecting ammonia comprising measuring the fluorescence of the sensor material; exposing the sensor material to a solution comprising ammonia; measuring the fluorescence change due to the ammonia; and determining the concentration of the ammonia.

The present invention also provides optical sensing devices comprising a pH sensitive fluorophore immobilized in a hydrophobic polymer, wherein the fluorophore reacts quantitatively with ammonia and the transducing moiety is neutrally charged when deprotonated; the polymer is coated on the surface of an optical component which is transparent to incident and emissive electromagnetic waves, optically connected to means for collecting radiant emission to measure the fluorescence indicative of the ammonia concentration.

The present invention provides ammonia sensors that are inexpensive and highly sensitive, yet also reversible. The pH indicator dyes used in the sensors are fluorophores which remain activated and protonated when combined with hydrophobic polymers. The sensors can be used in conjunction with sensors to detect other analytes as well.

DESCRIPTION OF ILLUSTRATIVE EMBODIMENTS

Figure 1:
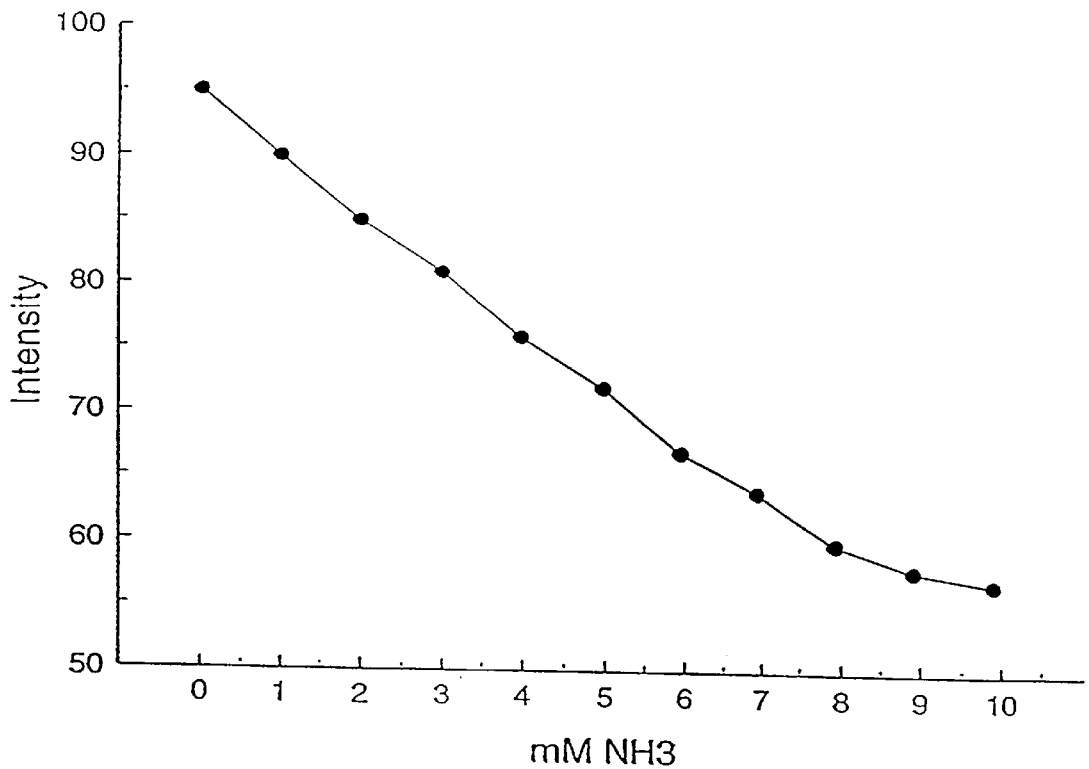
FIG. 1 shows the response of the ammonia sensor in units of fluorescence intensity, as a function of mM concentration of ammonia.

The present invention relates to sensors for the detection of ammonia. The sensors of the present invention comprise a fluorophore immobilized in a hydrophobic polymer, wherein the fluorophore can react quantitatively with ammonia and the transducing moiety is neutrally charged when deprotonated.

The transducing moiety is the ring or group of rings in the molecular structure of the pH sensitive fluorophore, which produces the fluorescence when radiated with the particular excitation energy required for excitation. This same segment of the molecule undergoes a resonance change due to protonation and deprotonation, and this change results in a change in the fluorescence which allows one to calibrate the fluorescence as a function of pH alteration. A substituent ring that is not involved in the pH based resonance change may be negatively charged when deprotonated; see e.g. the benzoic acid residue on rhodamine.

Fluorophores suitable in the sensors of this invention are fluorescent pH indicators wherein the transducing moieties are neutrally charged when deprotonated, and which exist in the protonated state in the microenvironment of the polymer. Additionally, the pH sensitive fluorophore should have a $pK_a$ that is more basic than the microenvironmental pH of the hydrophobic polymer. Such fluorophores include acridine orange:

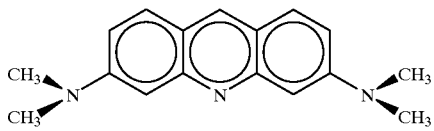

and rhodamine dyes:

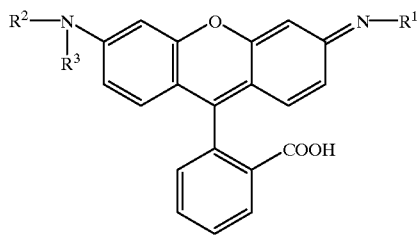

wherein $R^1$ and $R^2$ are independently an alkyl having between about 2 and 20 carbon atoms and $R^3$ is hydrogen or an alkyl having between about 2 and 20 carbon atoms. Acridine orange and rhodamine dye derivatives are preferred fluorophores. The modulation of the acridine fluorescence is generally measured with an excitation at 489 nm and emission at 540 nm, but can be excited at other wavelengths. A ratiometric readout can be achieved by exciting at two wavelengths and generating a ratio of the two emissions as a function of ammonia. The modulation of fluorescence of a rhodamine derivative, wherein $R^1$ and $R^2$ are both $C_{18}H_{37}$, is generally measured with an excitation at 530 nm and emission at 590 nm.

Detection of ammonia is based on changes in the fluorescence spectrum of the fluorophore upon deprotonation, as shown in the reaction below:

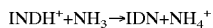

Polymers useful in the present invention are hydrophobic polymers, preferably a polymer in which the fluorophore is at least partially soluble. The polymers are permeable to ammonia gas, nonpolar and optically transparent in the visible region. Such polymers include but are not limited to: polystyrene, polyurethane, poly(ethyl cellulose), polydienes such as poly(1,3-butadiene), butadiene-acrylonitrile copolymer, poly(dimethylbutadiene), and polyisoprene, polyalkenes such as polyethylene, isobutane-isoprene copolymer, poly(4-methylpentene), polypropylene, polyethylmethacrylate, polytetrafluoroethylene, poly(vinyl alcohol), poly(vinyl chloride), and polyoxymethylene, cellulose and cellulose derivatives, such as cellulose hydrate, cellulose acetate, cellulose nitrate, ethyl cellulose, and cellulose ethyl methacrylate, polymethacrylates such as poly (methyl methacrylate) and poly(ethyl methacrylate) as well as polysiloxanes, polyesters and polycarbonates. Preferred polymers are ethyl cellulose and polyurethane.

The fluorophore and hydrophobic polymer are combined to form a fluorescent polymer. The signal intensities of the fluorescent polymer are high as the fluorophore is very soluble in the organic media of the polymer, and no quenching of fluorescence occurs (as in U.S. Pat. No. 5,506,148) due to the lack of negative charges on the fluorescing moiety of the molecule. Upon exposure to ammonia, the fluorescence of the fluorescent polymer decreases, consistent with the fluorophore becoming deprotonated with the formation of ammonium ion in the fluorescent polymer. This sensor response is reversible when the source of ammonia is withdrawn, and the ammonia in the sensor diffuses out of the membrane.

The sensor material can be prepared by dissolving the fluorophore and polymer in a suitable solvent, such as an alcohol, toluene, tetrahydrofuran or other organic solvent known in the art for dissolving the hydrophobic polymer. In general, the amount of fluorophore to be used should be between about 0.05% and 0.5% of the total mass. The fluorophore is preferably uniformly distributed throughout the resulting fluorescent polymer.

A membrane or film can then be formed from the dissolved fluorescent polymer by any suitable method known in the art, such as spincoating or brushing onto a non-reactive substrate, such as glass, plastic or ceramic. Alternatively, the fluorophore can be covalently attached to the polymer, as described in U.S. Pat. No. 5,005,572.

An onium compound can optionally be added to the fluorescent polymer. The onium compound adjusts the microenvironment pH of the fluorescent polymer to enhance the sensitivity to ammonia. Onium compounds include ammonium, phosphonium and pyridinium compounds. Examples of suitable onium compounds include tetrabutylammonium hydroxide, tetrabutylammonium chloride, cetyltrimethylammonium bromide, tetrabutylammonium hydrogen sulfate, tetrabutylammonium trifluoromethane, tetrabutylammonium acetate, tetraethylammonium bromide, tetraethylammonium p-toluenesulphoate, phenyltrimethylammonium chloride, benzyltrimethylammonium bromide, tetra-n-propylammonium bromide, benzyltriethylammonium tetrafluoroborate, n-dodecyltrimethylammonium bromide, tetraphenylphosphonium chloride, n-hexadecylpyridinium bromide, triphenyl phosphonium chloride, tetrabutylphosphonium bromide and hexadecyltrimethylammonium hydroxide. Preferred onium compounds are quaternary ammonium compounds, such as tetrabutylammonium hydroxide.

Since the polymer is hydrophobic, the membrane can serve as its own protective barrier against bulk pH effects. However, one can modify diffusion or permeable dependent response properties by addition of a second coating over the fluorescent polymer. This second coating can be prepared from the same polymer, or from a polymer of different structure but compatible with the first coating to facilitate deposition. Hydrophobic polymers previously mentioned can used in the second coating as well. Additionally, the second coating can serve to immobilize or link another sensor component, such as an enzyme. When an enzyme is used as an additional sensor component, the polymer used for the second coating is preferably hydrophilic.

The fluorescent polymers can also be used as transducer coatings for optical sensors. Traditional optical sensors for $CO_2$, $NH_3$, and other species detected via a pH modulated transducer are based on the Sevefinghaus model (Severinghaus, J. W.; Bradley, A. F. J. *Appl. Physiol.*, 13: 515 (1958)) where one has a transducer layer containing a pH sensitive fluorophore or chromophore, coated with a hydrophobic cover membrane material, such as a siloxane based polymer (Munkholm, C., Walt, D. R., Milanovich, F. P., *Talanta*, 35:109–112 (1988)). A difficulty inherent with Severinghaus sensors is their potential to fail due to pinhole leaks in the cover membrane. Sensors prepared by the instant invention will provide quantitative measurements of ammonia levels via a modulation of the microenvironment of the fluorophore within the polymer. Since these sensor microenvironments are dispersed throughout the polymer, preparing such a sensor requires only a single application of the membrane material, and this single membrane configuration makes the problem of pinhole leaks irrelevant. The sensors are not responsive to changes in the bulk pH, indicating that the transducer microdomains are sequestered from the sample. This sensor can be used in a system which measures reflected surface fluorescence as well as in a system measuring an evanescent wave signal.

An advantage of optical sensors is their ability to resolve information from different analytes via their discrete wavebands. In this way one could couple an ammonia sensor together with a sensor for a different analyte in the same membrane, but collect the readout information at separate wavelengths. The sensor microdomains would be populated by multiple transducers but the chemistry and signal processing would be conducted as if the sensors were in separate layers. In such a multiple-analyte sensor, the transducer for the non-ammonia analyte may be a polyanionic dye, such as those described in U.S. Pat. No. 5,506,148.

The sensor material can be used to monitor ammonia in biological samples, bioreactors, environmental samples and any sample where it is desirable to measure the level of ammonia. The sensor material can also be used to monitor enzymatic reactions during which ammonia is released or consumed. Examples of such reactions include determination of urea by measuring the ammonia released from the reaction of urea with urease and the determination of creatinine from the reaction of creatinine with creatinine deiminase. The sensor material can also be used to monitor the binding of antigens to antibodies.

Using the methods of this invention one can prepare extremely thin sensor films, approximately 0.5 to 5 $\mu$m thick, having a detectable level of fluorescence. Such thin films can provide an unusually rapid response time and be ideal for coating planar sensors used in evanescent wave methods of detection where one wants a fluorescent coating to be within the same dimensions as the propagating wave. Sensors prepared with this method will not be affected by pinhole leaks as the sensor material is continuous in the coating. These sensor films also have a longer shelflife due to their lack of an aqueous layer, which would be susceptible to dehydration.

The following examples are included to demonstrate preferred embodiments of the invention. (Comparative examples are included to show cases in which the fluorescence was quenched, and, therefore, could not be used as a sensor.) It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

A 10% solution of ethyl cellulose was prepared. A $10^{-3}$ M solution of acridine orange dye was prepared by mixing 15 mg in 40 mL of ethanol and 1 mL was added to 10 mL of polymer solution. The polymer/dye solution was divided into two aliquots and tetrabutylammonium hydrogen sulfate was added to one aliquot to give a $10^{-2}$ M concentration. The solutions were sonicated for 30 minutes and coatings were then spincoated onto glass substrates.

Excitation and emission spectra were generated and strong fluorescence bands were measured in the wavelength region expected for this dye the coatings prepared without the tetrabutylammonium hydrogen sulfate had slightly higher intensities.

The coatings were than tested for ammonia response using $NH_4^+Cl^-$ solution of 0.001 and 0.1 M, to which NaOH was added to deprotonate the ammonium to ammonia. When the coating was exposed to the ammonia solutions the fluorescence decreased in proportion to the concentration of ammonia. (See FIG. 1, where the response of the ammonia sensor in units of fluorescence intensity as a function of mM concentration of ammonia is shown.) Further, the response was reversible.

The coatings with and without tetrabutylammonium hydrogen sulfate were sensitive to ammonia. Since it is important that the coating not be affected by pH changes in solution, the coatings were exposed to buffers of pH 8, 9, 10 and 11. No response to pH of the solution was observed.

EXAMPLE 2

The above experiment was repeated with the only difference being the application of a thicker coating due to higher polymer concentration. The coatings were approximately 15 $\mu$m thick. The fluorescence intensity increased threefold, and the coating remained responsive to ammonia but unresponsive to changes in the pH of the solution.

EXAMPLE 3

Figure 2:
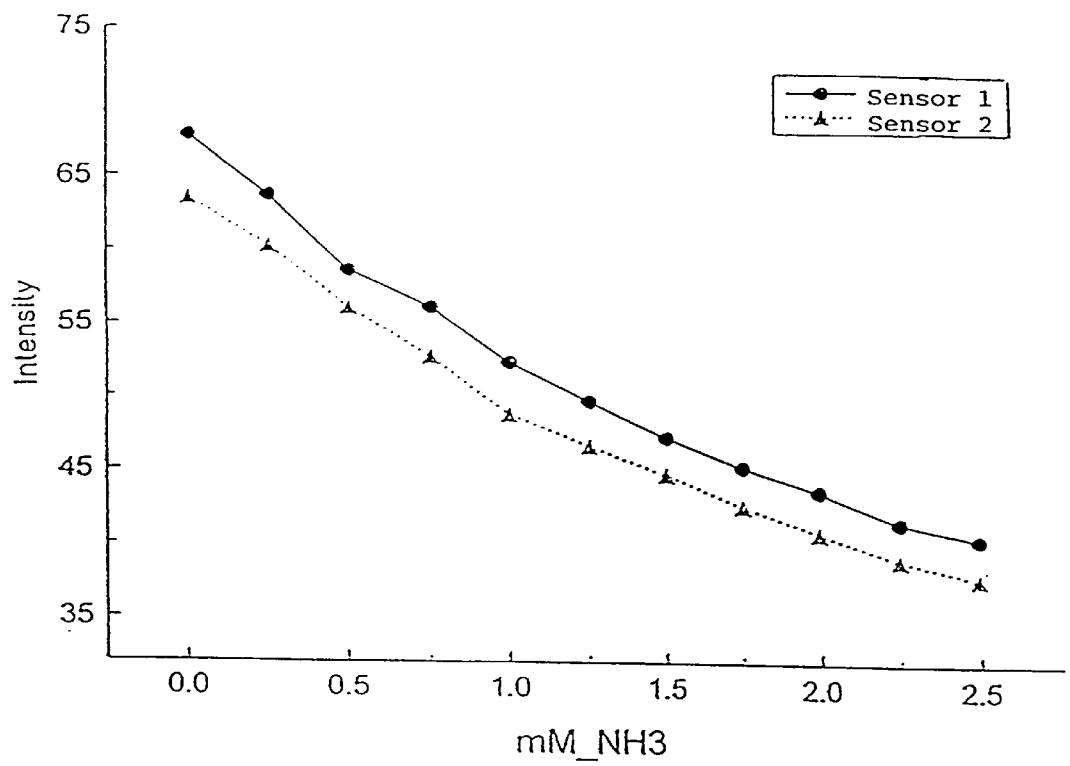
FIG. 2 shows a similar response for sensors containing ultra bright ammonia hydroxide.

Acridine orange was added to a 10% ethyl cellulose solution to give a final concentration of $10^{-3}$ M. The solution was divided into five aliquots. To two of the aliquots, tetrabutylammonium hydrogen sulfate was added to give final concentrations of $4\times10^{-3}$ M and $8\times10^{-3}$ M. To two of the aliquots, tetrabutylammonium hydroxide was added to give final concentrations of $4\times10^{-3}$ M and $8\times10^{-3}$ M. The solutions were sonicated for one hour, and coatings were then prepared by spincasting onto glass substrates. All of the formulations produced coatings that were sensitive to ammonia. The coatings prepared with tetrabutylammonium hydroxide displayed more sensitivity to the low concentrations of ammonia than the other two formulations. (Compare the increased sensitivity of these formulations, Sensor 1 and Sensor 2, in FIG. 2 vs. the samples without tetrabutylammonium hydroxide in FIG. 1.)

EXAMPLE 4

A 10% solution of ethyl cellulose was prepared and divided into three aliquots, and each was adjusted to a different concentration of acridine orange: A=$5\times10^{-4}$ M, B=$2\times10^{-4}$ M. The solutions were sonicated for one hour, and coatings were then prepared by spincasting onto glass substrates. All of the formulations produced coatings that were sensitive to ammonia, and the absolute intensities reflected the concentration of the dye in the formulation, with the A solution producing the most fluorescent coatings.

EXAMPLE 5

Acridine orange was added to a 10% solution of ethyl cellulose to give $5\times10^{-4}$ M. The solution was divided into seven aliquots and tetrabutylammonium hydroxide was added to six of the polymer solutions to give the following concentrations: A=0, B=$5\times10^{-4}$ M, C=0.001 M, D=0.0015 M, E=0.002 M, F=0.0025 M and G=0.005 M. The solutions were sonicated and coatings were prepared by spincasting onto glass substrates. All of the coatings were fluorescent. The response to ammonia varied with the concentration of tetrabutylammonium hydroxide with the G formulation showing the most sensitivity to ammonia.

EXAMPLE 6

A 7% ethyl cellulose solution was prepared. A monosubstituted ($C_{18}H_{37}$) rhodamine was added to give a final concentration of $7.25\times10^{-5}$ M. Membranes were prepared by spincoating onto glass substrates. Excitation spectra were generated with an emission maximum at 590 nm and emission spectra were generated with an excitation maximum at 530 nm. The sensors were quantitatively responsive to ammonia solutions of 5 mM and 9 mM.

COMPARATIVE EXAMPLE 1

A 10% solution of ethyl cellulose was prepared in toluene:ethanol (8:2). The dye hydroxypyrenetrisulphonic acid (HPTS), which does not have a neutrally charged fluorescence moiety when deprotonated, was added to give a final concentration of $5\times10^{-5}$ M and the solution was divided into three aliquots. Cetyltrimethylammonium bromide (CTAB) was added to each to give final concentrations of 5, 12.5 and 25 mM. Membranes were prepared by spincoating onto glass substrates. Excitation spectra indicated that the fluorescence was quenched in the samples with and without the CTAB.

COMPARATIVE EXAMPLE 2

A 10% solution of ethyl cellulose was prepared. HPTS was added to give a final concentration of $5\times10^{-5}$ M, and the solution was divided into ten aliquots. Four quaternary ammonium compounds were screened, at two concentrations for each (10 and 20 mM): 1) tetrabutylammonium hydrogen sulfate, 2) tetrabutylammonium trifluoromethane sulphonate, 3) tetrabutylammonium hydroxide, and 4) tetrabutylammonium acetate. Membranes were prepared by spincoating onto glass substrates. Excitation spectra indicated that the membrane prepared with tetrabutylammonium hydrogen sulfate supported the dye in the protonated state but the intensities were so low that the fluorescence appeared to be quenched.

COMPARATIVE EXAMPLE 3

The preceding experiment was repeated using the tetrabutylammonium hydrogen sulfate, with the HPTS concentration increased to $10^{-4}$ M in the membrane, but the fluorescence was again quenched.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are chemically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An ammonia sensor material comprising a pH-sensitive fluorophore immobilized within a hydrophobic polymer, said immobilization having taken place in the presence of an organic solvent, wherein the fluorophore is protonated within the polymer in the absence of ammonia, can react quantitatively with ammonia, and has a transducing moiety comprising at least one ring in a molecular structure of the fluorophore that fluoresces when irradiated, the transducing moiety becoming neutrally charged when deprotonated, wherein the presence of ammonia is indicated by a change in fluorescence directly resulting from deprotonation of the fluorophore.

2. A method for measuring ammonia comprising:

measuring the fluorescence of the ammonia sensor material of claim 1, in the absence of ammonia;

exposing the ammonia-sensor material to a solution comprising ammonia;

measuring the fluorescence change resulting directly from deprotonation of the transducing moiety of the fluorophore, following exposure to the ammonia; and determining the concentration of the ammonia from the fluorescence change.

3. An optical sensing device for measuring ammonia concentration, comprising:

an optical component transparent to incident and emissive electromagnetic waves, optically connected to means for collecting radiant emission; and on a surface of the optical component, a pH-sensitive fluorophore immobilized within a hydrophobic polymer, said immobilization having taken place in the presence of an organic solvent, wherein the fluorophore is protonated within the polymer in the absence of ammonia, can react quantitatively with ammonia and has a transducing moiety comprising at least one ring in a molecular structure of the fluorophore that fluoresces when irradiated, the transducing moiety becoming neutrally charged when deprotonated, wherein the presence of ammonia is indicated by a change in fluorescence directly resulting from deprotonation of the fluorophore.

* * * * *